United States Patent [19]

Shortridge

[11] Patent Number: 4,619,994
[45] Date of Patent: Oct. 28, 1986

[54] BENZENEAZO POLYNUCLEAR AROMATIC OR HETEROAROMATIC AMIDINE COMPOUNDS CONTAINING AMIDINE SUBSTITUENTS

[76] Inventor: Douglas Shortridge, 36, Parkside Road., Leeds, West Yorkshire LS6 4QG, England

[21] Appl. No.: 759,493

[22] Filed: Jul. 25, 1985

Related U.S. Application Data

[63] Continuation of Ser. No. 488,717, Apr. 26, 1983, abandoned.

[51] Int. Cl.$^4$ .................. C07C 107/00; C07C 107/04; C07C 107/08; A61K 31/655
[52] U.S. Cl. ...................................... 534/738; 534/653
[58] Field of Search .................. 534/653, 738; 514/150

[56] References Cited

FOREIGN PATENT DOCUMENTS 1244877 9/1971 United Kingdom ................ 534/738

*Primary Examiner*—Floyd D. Higel
*Attorney, Agent, or Firm*—Bert J. Lewen; Henry Sternberg

[57] ABSTRACT

A compound, useful as an anti-cancer drug or agent, having the formula

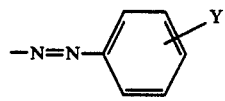

where X represents a polynuclear aromatic or heteroaromatic hydrocarbon having between two and four fused rings which may be substituted by hydroxyl, amino, alkylamino, alkoxy or halogeno, $R_1$ represents:

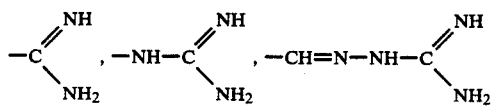

where y represents one member selected from:

$$-C\overset{NH}{\underset{NH_2}{\diagdown}} \quad , \quad -NH-C\overset{NH}{\underset{NH_2}{\diagdown}} \quad , \quad -CH=N-NH-C\overset{NH}{\underset{NH_2}{\diagdown}}$$

or alkylated derivatives thereof, and $R_2$ represents hydrogen or $R_1$, an acid addition salt of said compound, a nitrogen oxide derivative of said compound in the case where it contains a ring nitrogen atom or atoms, and a quaternary salt of said compound in the case where it contains a ring nitrogen atom or atoms.

5 Claims, No Drawings

BENZENEAZO POLYNUCLEAR AROMATIC OR HETEROAROMATIC AMIDINE COMPOUNDS CONTAINING AMIDINE SUBSTITUENTS

This application is a continuation of application Ser. No. 488,717, filed Apr. 26, 1983, now abandoned.

This invention relates to chemical compounds useful for the purpose of cancer research and comprises a group of such compounds which exhibit activity against cancer in experimental animals.

In the field of anti-tumour compounds and compounds active against leukaemia, research is directed towards the discovery of compounds having a selective action against the tumour cell, and usually makes progress by the screening of large numbers of compounds which are chemically similar to compounds of known and established medical value. The present invention is the outcome of a theoretical approach to this subject based, inter alia, on considerations of selective bonding between the tumour cell and a compound of specific size, shape and electrical charge distribution, which can lead to the eventual destruction or control of the tumour cell.

The present invention provides a compound of the formula

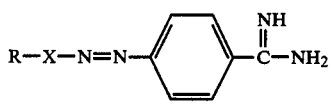

where X is a polynuclear aromatic or heteroaromatic group having from 2 to 4 fused rings which may be substituted by hydroxyl and $C_1$-$C_2$ alkyl; and R is hydrogen or a group of the formula

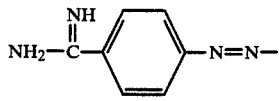

and an acid addition salt of said compound.

The products are desirably prepared and used as the acid addition salts of any appropriate inorganic or organic acid. Materials carrying a second basic phenyl azo grouping as a substituent are especially preferred, as also are those compounds possessing a total of four or five aromatic or heteroaromatic ring structures.

The azo compounds are made by methods well known to those skilled in the art. It is most convenient to do so by coupling the diazonium salt of an aniline containing one of the desired basic groupings with a polynuclear aromatic or heteroaromatic hydrocarbon carrying one or more activating substituents to make coupling possible such as for example hydroxyl, amino or alkylamino. The nature of the activating grouping is not critical.

Compounds in accordance with the invention are active against the P388 leukaemia in mice and may be administered by injection, or orally, at a dose rate of, for example, 20 to 50 mg per kilogram of animal per day.

The survival time of mice treated with these substances has been extended typically by some 50% and much longer in some cases as compared with untreated mice after implantation of the leukaemia for the control mice.

It will be appreciated that the invention also embraces pharmaceutical compositions containing any of the aforementioned compounds as the active constituent and methods for preparing such compounds in a form suitable for administration.

The invention will now be further described with detailed examples of the preparation of typical compounds in the form of hydrochloride salts but these examples do not limit the invention thereto.

EXAMPLE I

Preparation of the compound of the formula:

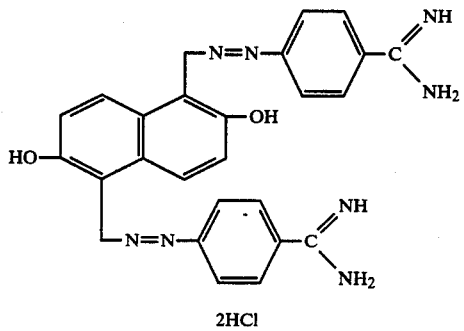

2.0 grs. para amino benzamidine dihydrochloride is dissolved in 50 ml water and 1.0 ml concentrated hydrochloric acid and diazotised by addition of 0.7 gr sodium nitrite dissolved in 5 ml water desirably keeping all at under 10° C. Excess nitrous acid is removed by careful addition of sulphamic acid, testing with starch iodide paper. The diazonium solution is then coupled with 1.0 gr 2.6 dihydroxy naphthalene dihydrate dissolved in 100 ml water with 0.4 gr sodium hydroxide and 10 ml pyridine, all at under 10° C., maintaining the pH value at approximately 8. When coupling is complete the resultant mixture is adjusted to a pH value of approximately 6 with hydrochloric acid, though this is not critical. The desired product is salted out with brine, washed well with ice cold water, and dried.

EXAMPLE II

Preparation of the compound of the formula:

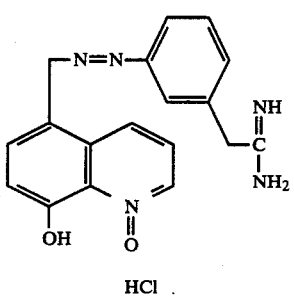

2.0 grs. meta amino benzamidine dihydrochloride are diazotised and coupled with 1.6 grs. 8 hydroxy quinoline N oxide as in Example I.

EXAMPLE III

Preparation of the compound of the formula:

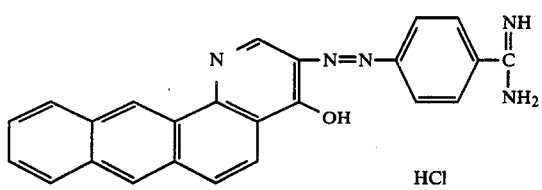

HCl

1' aza 4' hydroxy 1.2 benzanthracene is made by allowing 2.9 grs 1-amino anthracene and 3.5 ml oxalacetic ester to stand for 48 hours over concentrated sulphuric acid in a vacuum desiccator.

The product is then added slowly to 50 ml light mineral oil heated to 250° C. and kept at that temperature for about 30 minutes. The cooled product is filtered off and washed with benzene. The product is then hydrolysed by boiling with 5% caustic soda solution for two hours followed by neutralisation with hydrochloric acid. The product is then separated by filtration and dried. When heated slowly to above its melting point carbon dioxide is evolved and the desired product is obtained.

It is purified by dissolving in dilute caustic soda solution, filtering, neutralising with dilute hydrochloric acid, filtering, washing and drying. 1.25 grs of this material are dissolved in 40 ml pyridine and added to 200 ml water containing 0.75 gr sodium hydroxide all at under 5° C. This is coupled with 1.25 diazotised para amino benzamidine dihydrochloride, at under 5° C., acidified and separated, all as in Example I.

EXAMPLE IV

Preparation of the compound of the formula:

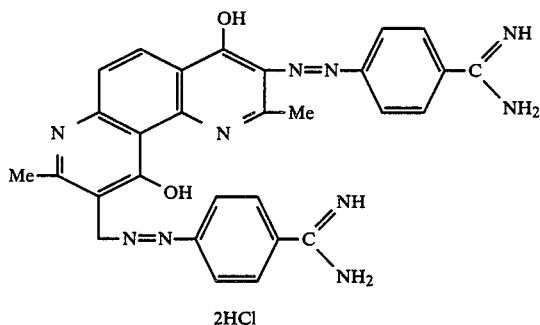

2HCl 1.5 diaza 2.6 dimethyl 4.8 dihydroxy phenanthrene is made by reacting 1.5 grs meta phenylene diamine and 4.0 grs ethyl acetoacetate with 20 grs tetra phosphoric acid at 170° C. for 1 hour. The mixture is poured into water, neutralised with caustic soda, filtered, washed, and dried at a low temperature. 1.1 grs of this product are dissolved in 10 ml pyridine and diluted with 50 ml water and sodium hydroxide added to bring the pH value to approximately 8.

2.0 grs. para amino benzamidine dihydrochloride in 20 ml water are diazotised and coupled with the above solution, keeping the pH value at approximately 8 and the temperature at under 5° C. When the reaction is complete the mixture is acidified to a pH value of approximately 6 with hydrochloric acid and the desired product salted out with brine. The precipitate is filtered off, washed well with ice cold water, and dried.

EXAMPLE V

Preparation of the compound of the formula:

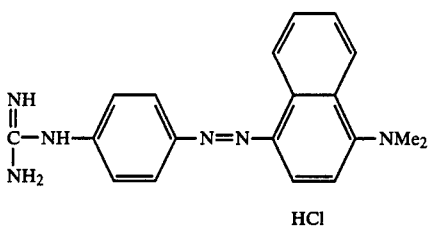

HCl 3.0 grs. para acetylamino phenylguanidine are hydrolysed by heating for 1 hour on the steam bath with 20 ml water and 5 ml concentrated hydrochloric acid. After cooling to under 5° C. 0.4 gr sodium nitrite dissolved in 5 ml water at under 5° C. is added. After removal of excess nitrous acid with sulphamic acid the solution is coupled with 2.0 grs N—N dimethyl-1-napthylamine dissolved in 25 ml dimethyl formamide and 50 ml water and acidified with hydrochloric acid to bring to a pH value of about 4. After coupling the desired product is salted out with brine, filtered off, washed well with water and dried.

EXAMPLE VI

Preparation of the compound of the formula:

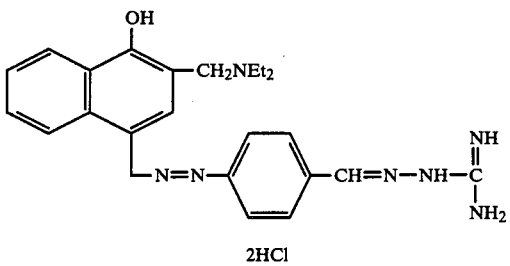

2HCl 2.0 grs para amino benzal amino guanidine in 20 ml water are diazotised and coupled with 2.0 grs 2-diethyl aminomethyl 1-naphthol in 100 ml water and 10 ml pyridine brought to a pH value of about 8, as in Example I.

EXAMPLE VII

Preparation of the compound of the formula:

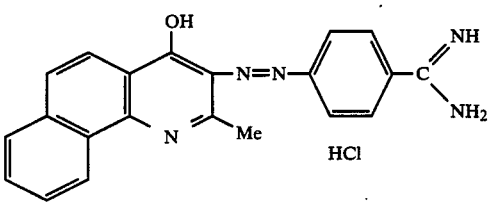

HCl 1.1. grs para amino benzamidine dihydrochloride in 15 ml water are diazotised in the standard manner and coupled with 1.0 gr 2-methyl 4-hydroxy 7.8 benzquinoline (Mallams & Israelstam J. Org. Chem. 1964-3548) in 10 ml pyridine and 50 ml water at a pH value of about 8, all as in Example IV.

EXAMPLE VIII

Preparation of the compound of the formula:

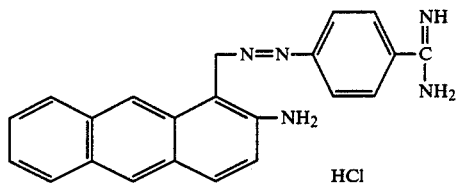

1.0 gr of 2-amino anthracene is dissolved in 20 ml dimethyl formamide. 100 ml water is added together with sufficient hydrochloric acid to bring the pH value to approximately 4 and cooled to under 5° C.

1.2 grs para amino benzamidine dihydrochloride are diazotised in the standard manner and coupled with the amine.

When coupling is complete the pH value is adjusted to about 6 although this is not critical, and the desired product removed by filtration, washed well with water and dried.

EXAMPLE IX

Preparation of the compound of the formula:

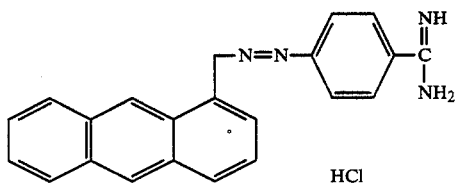

1.0 gr of the product of Example VIII is dissolved in 10 ml dimethyl formamide and 50 ml water and 1.5 ml concentrated hydrochloric acid. Diazotisation is effected by adding 0.4 gr sodium nitrite dissolved in 10 ml water all at under 5° C. The solution is then mixed with a solution of 1.0 gr hydroquinone in 20 ml water and left for 24 hours at about 20°-25° C. The product is separated by filtration, washed well and dried.

EXAMPLE X

Preparation of the compound of the formula:

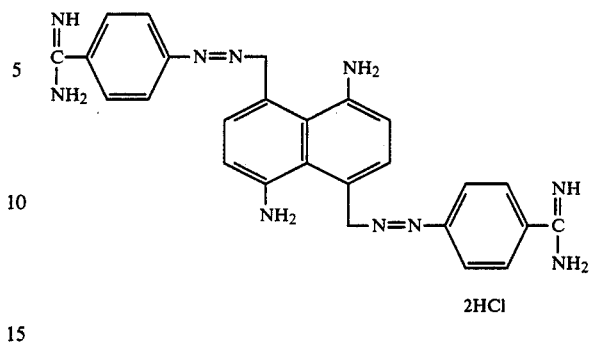

2.2 grs para amino benzamidine dihydrochloride are diazotised and coupled with 0.8 gr 1.5 diamino napthalene as in Example VIII.

I claim:

1. A compound of the formula

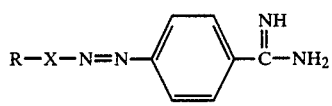

where X is a polynuclear aromatic or heteroaromatic group having from 2 to 4 fused rings which is unsubstituted or substituted by hydroxyl or $C_1$-$C_2$ alkyl; and R is hydrogen or a group of the formula

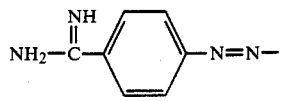

or an acid addition salt of said compound.

2. A compound of the formula

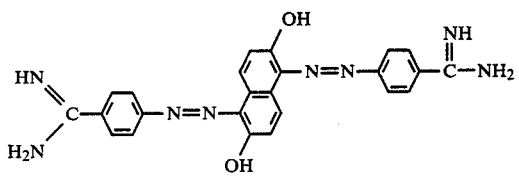

or an acid addition salt thereof.

3. A compound of the formula

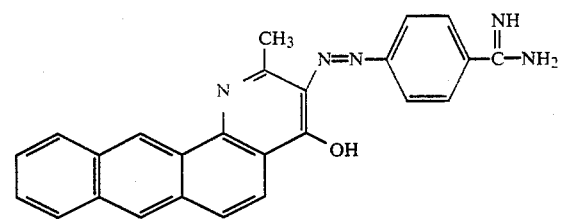

or an acid addition salt thereof.

4. A compound of the formula

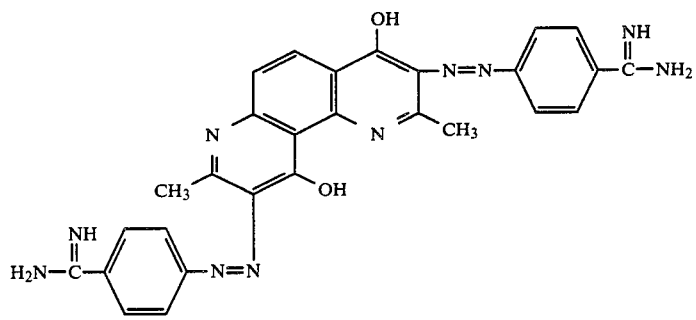
or an acid addition salt thereof.
5. A compound of the formula
or an acid addition salt thereof.